US012692292B2

(12) United States Patent
Skaar et al.

(10) Patent No.: US 12,692,292 B2
(45) Date of Patent: Jul. 28, 2026

(54) MOLECULAR STRATEGY TO PROTECT AGAINST DESICCATION

(71) Applicant: Vanderbilt University, Nashville, TN (US)

(72) Inventors: Eric P Skaar, Nashville, TN (US); Erin Green, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 708 days.

(21) Appl. No.: 18/006,139

(22) PCT Filed: Jul. 20, 2021

(86) PCT No.: PCT/US2021/042445
§ 371 (c)(1),
(2) Date: Jan. 19, 2023

(87) PCT Pub. No.: WO2022/020397
PCT Pub. Date: Jan. 27, 2022

(65) Prior Publication Data

US 2023/0287059 A1 Sep. 14, 2023

Related U.S. Application Data

(60) Provisional application No. 63/054,140, filed on Jul. 20, 2020.

(51) Int. Cl.
*C07K 14/21* (2006.01)
*C12N 1/20* (2026.01)
*C12N 15/82* (2006.01)

(52) U.S. Cl.
CPC .............. *C07K 14/212* (2013.01); *C12N 1/20* (2013.01); *C12N 15/8201* (2013.01); *C12N 2510/00* (2013.01)

(58) Field of Classification Search
None
See application file for complete search history.

(56) References Cited

U.S. PATENT DOCUMENTS 6,562,958 B1 5/2003 Breton et al.
2018/0169211 A1 6/2018 Moller et al.

FOREIGN PATENT DOCUMENTS

CN 106432451 2/2017

OTHER PUBLICATIONS

Green et al., "Bacterial hydrophilins promote pathogen desiccation tolerance", Cell Host Microbe 30(7): 975-987.e7. doi: 10.1016/j. chom.2022.03.019 Jul. 13, 2022.*

* cited by examiner

*Primary Examiner* — Anand U Desai
(74) *Attorney, Agent, or Firm* — Stites & Harbison PLLC; Mandy Wilson Decker

(57) ABSTRACT

A composition, transgenic organism, and method of protecting against desiccation or heat are provided. The composition includes a DtpA protein and a heterologous biologic. The transgenic organism includes the nucleic acid sequence encoding the amino acid sequence of SEQ ID NO: 1. The method includes contacting a heterologous biologic or organism with a DtpA protein.

10 Claims, 14 Drawing Sheets

Specification includes a Sequence Listing.

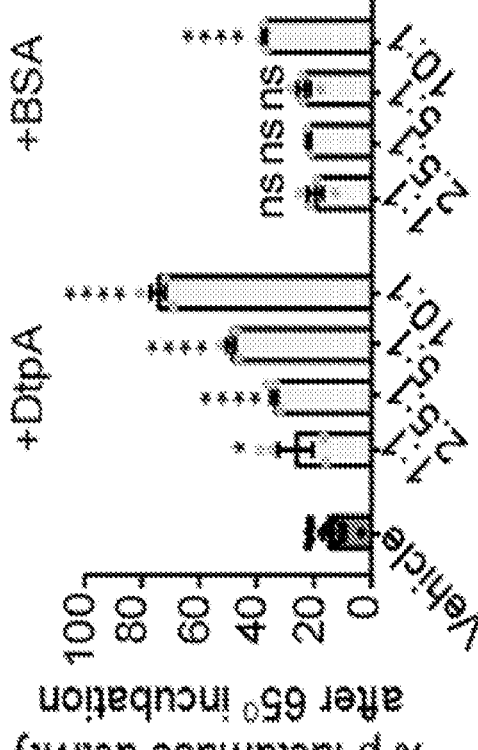
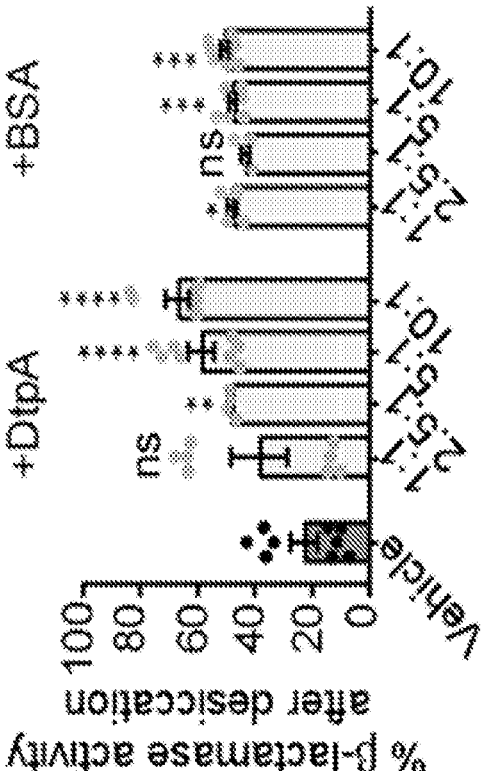
FIG. 3

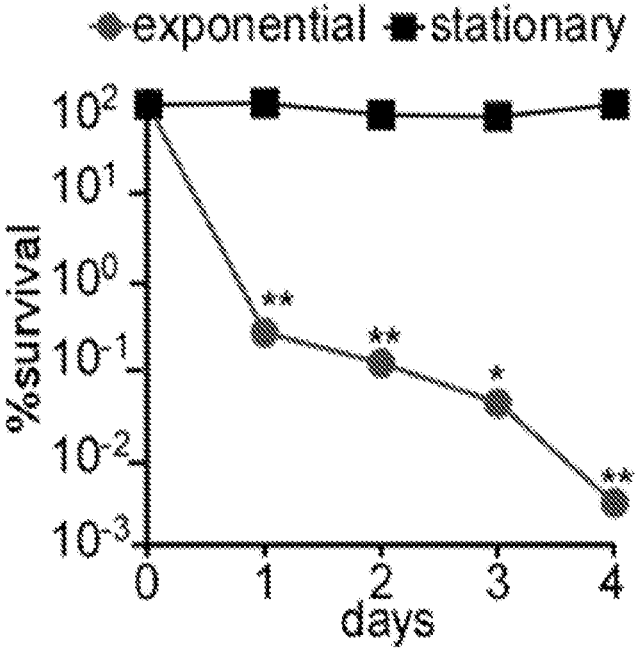
FIG. 5
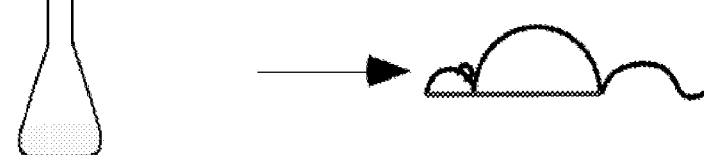
Stationary phase growth
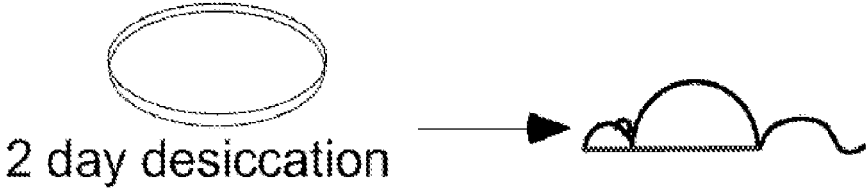
2 day desiccation
FIG. 6

Desiccate                    Sequence 90,000
insertion library 2 days
outgrowth 14 days
outgrowth outgrowth

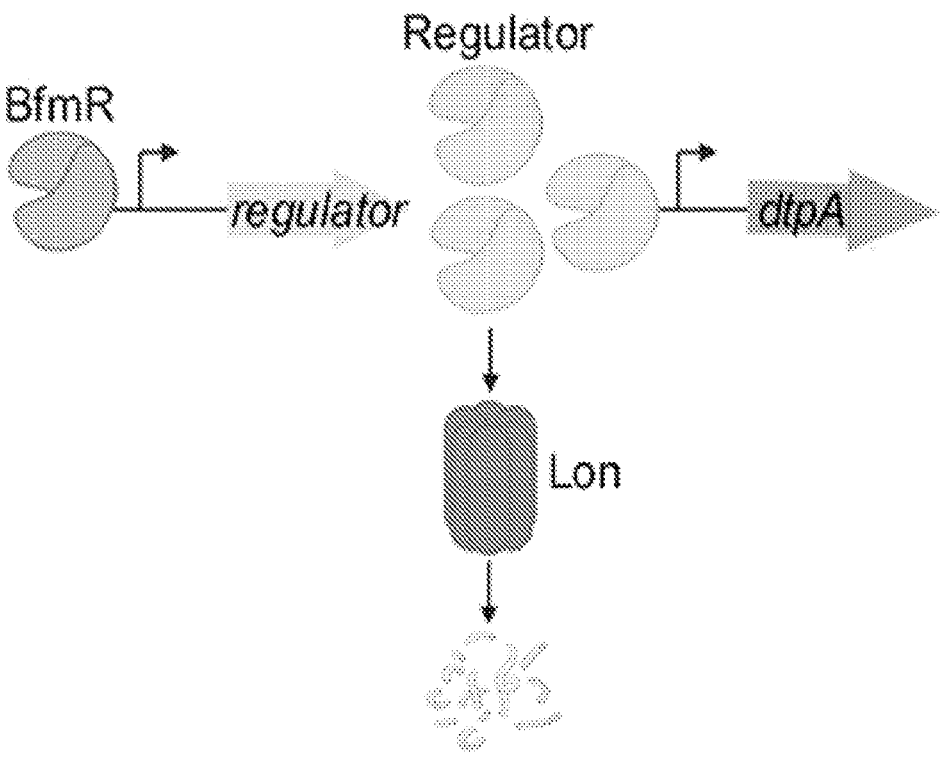
FIG. 21
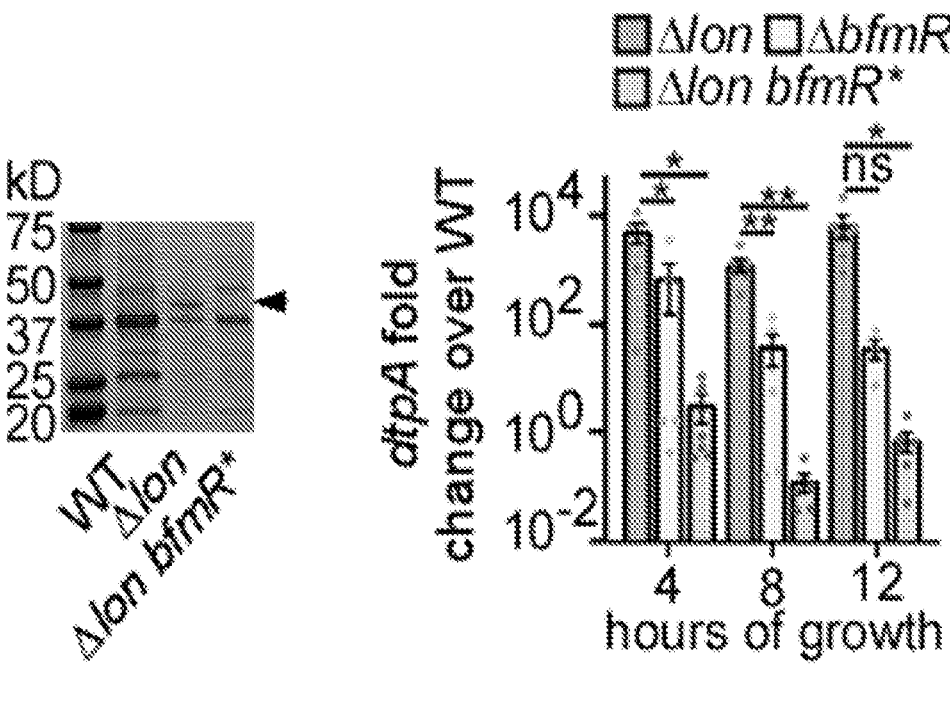
FIG. 22                          FIG. 23

MOLECULAR STRATEGY TO PROTECT AGAINST DESICCATION

RELATED APPLICATIONS

This application is a national stage application, filed under 35 U.S.C. § 371, of International Patent Application No. PCT/US2021/042445, filed Jul. 20, 2021, which claims the benefit of U.S. Provisional Application Ser. No. 63/054,140, filed Jul. 20, 2020, the entire disclosure of which is incorporated herein by this reference.

GOVERNMENT INTEREST

This invention was made with government support under grant number R01 AI101171 awarded by the National Institutes of Health (NIH). The government has certain rights in the invention.

SEQUENCE LISTING

The instant application contains a Sequence Listing which has been submitted in ASCII format via EFS-Web and is hereby incorporated by reference in its entirety. The ASCII copy of the Sequence Listing, which was created on Jul. 20, 2021, is named 11672N-21002WO.txt, and is 3.74 kilobytes in size.

TECHNICAL FIELD

The present-disclosed subject matter relates to articles and methods to protect against desiccation. In particular, the presently-disclosed subject matter relates to nucleic acid constructs and proteins that protect against desiccation, as well as methods of use thereof to protect against desiccation.

BACKGROUND

Many protein and live bacterial-based pharmaceuticals and therapeutics have limited shelf lives and are sensitive to loss of water, thus requiring their production and distribution to be carried out under refrigeration conditions. In some instances, this can result in reduced distribution, limited utility, and greater cost for these therapeutics.

A number of stabilizers and bulking agents can be used as additives in liquid formulations of protein-based therapeutics; however, these additives can have limited utility. For example, sugars such as mannitol, sorbitol, and trehalose can effectively stabilize proteins in solution, but are prone to crystallization during long-term storage as frozen solutions. Sucrose is more stable under freezing conditions, but it can induce physical changes or chemical degradation of proteins upon storage at higher temperatures. Other saccharide molecules, such as the disaccharide dextran, do not form sufficient water-substituting interactions with proteins because of steric hindrance, and are thus not suitable for protein stabilization. Freeze drying, or lyophilization, is commonly used to provide shelf stability to solid formulations of protein-based pharmaceuticals, as well as for stabilizing live-bacterial based therapeutics such as probiotics. However, this process has shortcomings, as it requires higher production costs, and can induce various chemical changes to proteins that can result in their denaturation, including oxidation and hydrolysis. Some additive agents can help to stabilize protein structures during freeze-drying; however, none of these agents work universally.

Accordingly, there remains a need for compositions and methods that stabilize proteins and other biological material.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a composition including a DtpA protein; and a heterologous biologic. In some embodiments, the DtpA protein is encoded by the sequence according to SEQ ID NO: 1. In some embodiments, the DtpA protein comprises at least 80% sequence identity to SEQ ID NO: 1. In some embodiments, the DtpA protein includes one or more mutations in a disordered part of the protein. In some embodiments, the disordered part of the protein includes amino acids 26-411. In some embodiments, the composition is solid. In some embodiments, the composition is liquid. In some embodiments, the heterologous biologic is selected from the group consisting of enzymes, food, vaccines, heterologous polypeptides, heterologous proteins, and combinations thereof. In some embodiments, the DtpA protein thereof is recombinantly added to the heterologous biologic. In some embodiments, the DtpA protein is exogenously added to the heterologous biologic.

Also provided herein, in some embodiments, is a transgenic organism comprising the nucleic acid sequence encoding the amino acid sequence of SEQ ID NO: 1. In some embodiments, the organism is a heterologous cell. In some embodiments, the heterologous cell is a plant cell. In some embodiments, the heterologous cell is an animal cell. In some embodiments, the organism is a heterologous organism. In some embodiments, the heterologous organism is a bacterium. In some embodiments, the heterologous organism is a tissue or organ. In some embodiments, the heterologous organism is a plant.

Further provided herein, in some embodiments, is a method of protecting against desiccation or heat, the method comprising contacting a heterologous biologic or organism with a DtpA protein. In some embodiments, the DtpA protein comprises the sequence of SEQ ID NO: 1.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consider-

Figure 1A:
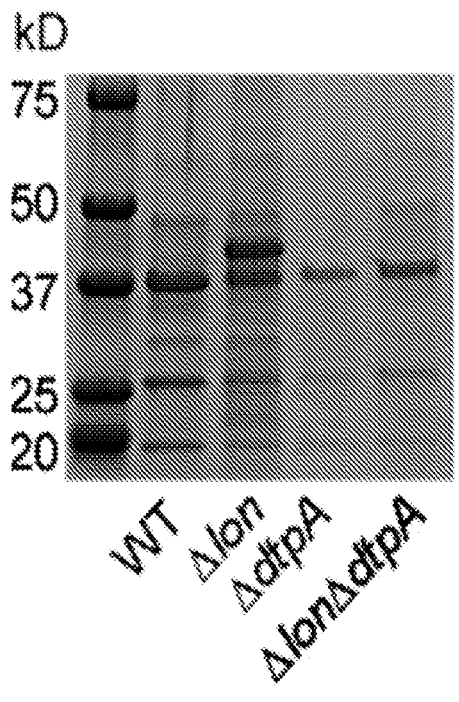
Figure 1B:
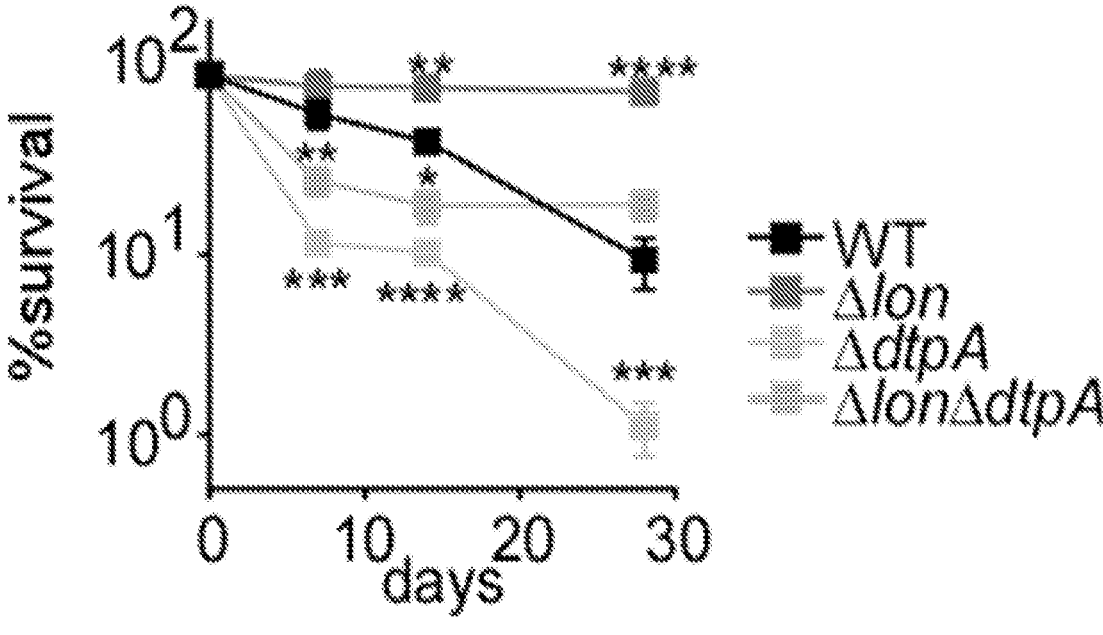

3 ation is given to the following detailed description thereof. Such detailed description makes reference to the following drawings, wherein:

FIGS. 1A-B show an image and graph illustrating that DtpA is essential for survival of desiccated *Acinetobacter baumannii*. (A) Insoluble protein fraction harvested from WT and mutant stationary phase cultures. DtpA is more abundant in a mutant strain lacking lon protease. (B) Desiccation tolerance of WT and mutant strains of *A. baumannii* over a period of 28 days. Desiccation tolerance was monitored by measuring viable bacteria at the indicated timepoints relative to the starting population. A Δlon strain is resistant to desiccation, while a ΔdtpA strain is more sensitive to desiccation than WT *A. baumannii*.

Figures 2A, 2B:
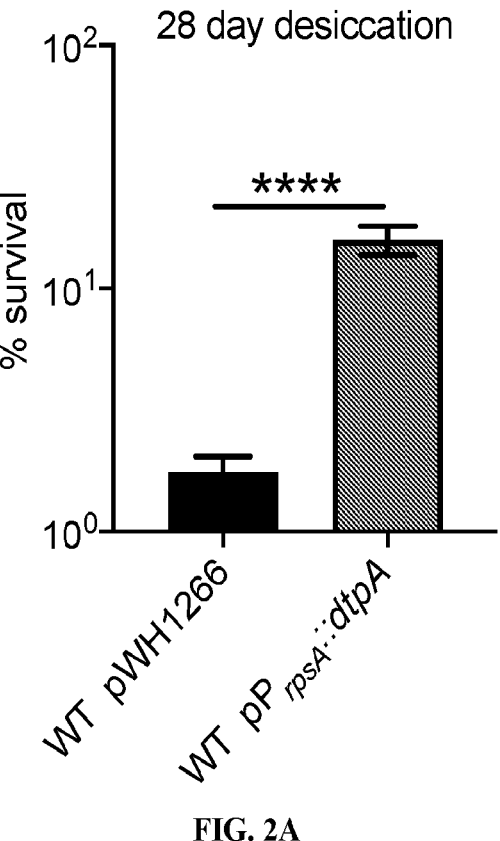

FIGS. 2A-B show graphs illustrating that overexpression of dtpA enhances bacterial desiccation tolerance. (A) Desiccation tolerance of WT *A. baumannii* constitutively expressing dtpA from the multicopy plasmid pWH1266 was monitored by measuring viable bacteria after 28 days of desiccation relative to an empty vector control. (B) The desiccation tolerance of *E. coli* DH5 heterologously expressing dtpA from the multicopy plasmid pBAD33 was monitored by measuring viable bacteria after 24 hours of desiccation relative to an empty vector control.

FIG. 3 shows a graph illustrating that recombinant DtpA protects enzymatic functions under desiccating conditions. 15 nM of TEM β-lactamase was air dried for 24 hours in the presence of recombinant DtpA or a vehicle control at the indicated molar ratios. Enzymatic activity of TEM β-lactamase was then monitored by measuring cleavage of the cephalosporin substrate nitrocefin. The percent activity remaining was determined by comparison to a control condition where proteins were stored at refrigeration temperature and mixed at equivalent ratios immediately prior to substrate addition.

Figure 4:
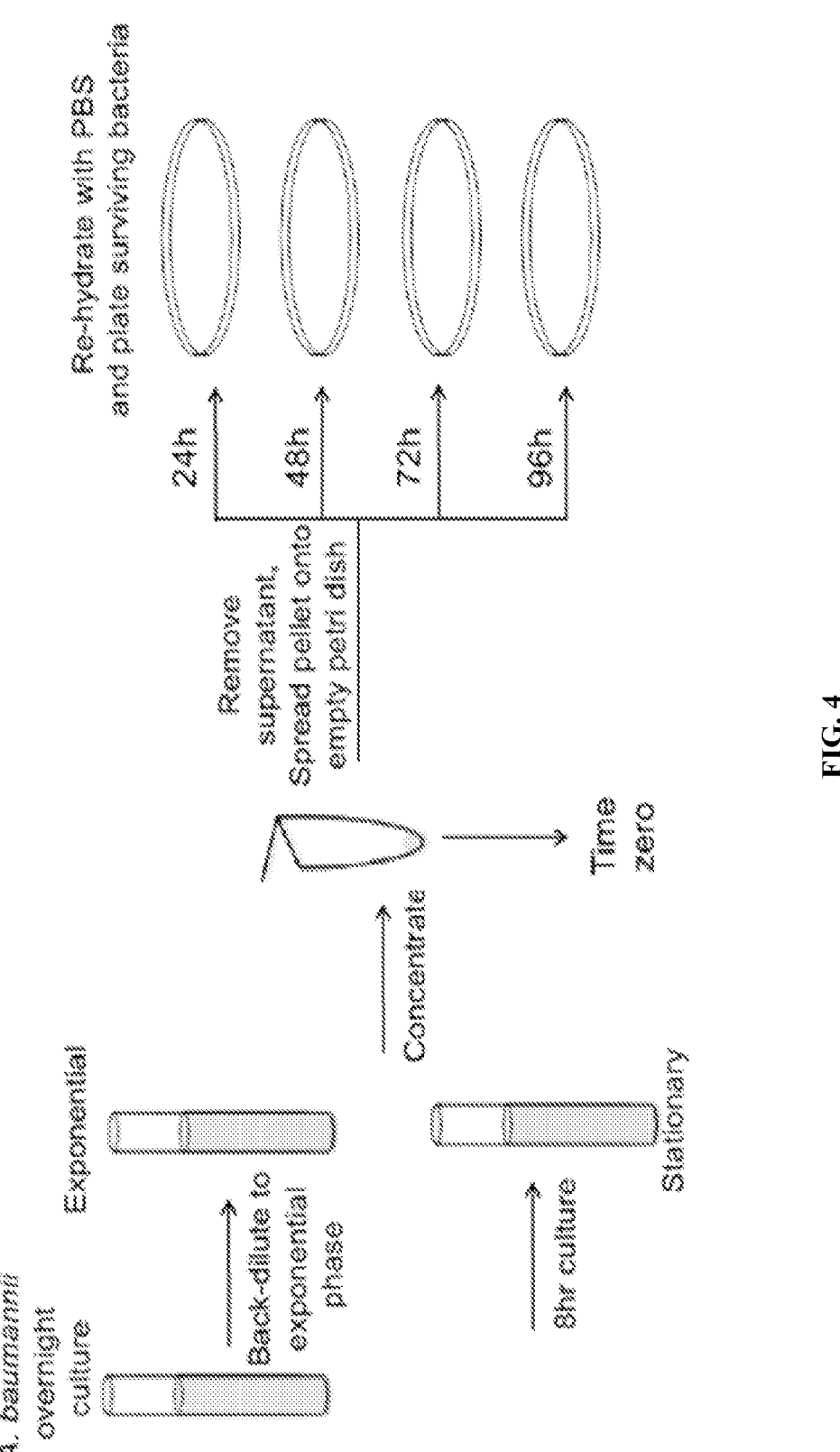

FIG. 4 shows a schematic illustrating a desiccation protocol.

FIG. 5 shows a graph illustrating how growth phase influences desiccation tolerance.

FIG. 6 shows a schematic of a desiccation murine intranasal infection model.

Figure 7:
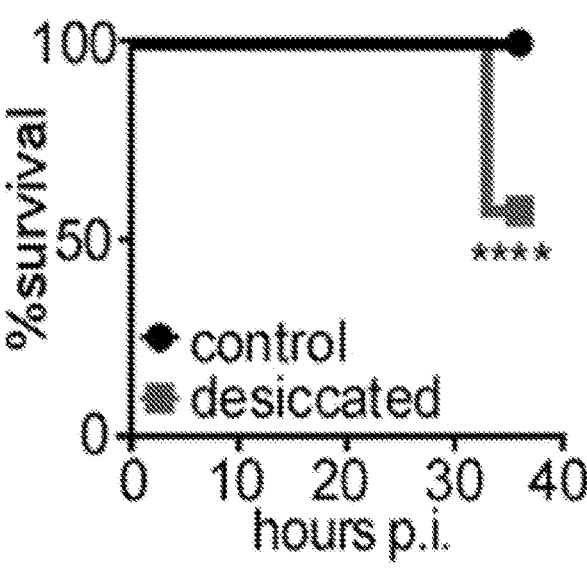

FIG. 7 shows a graph illustrating how desiccated *A. baumannii* is more virulent in a murine pneumonia model.

Figure 8:
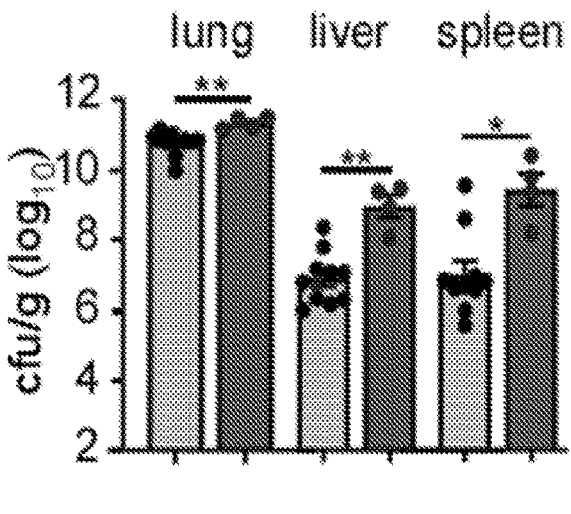

FIG. 8 shows a graph illustrating that bacterial loads are enhanced following infection with desiccated *A. baumannii*.

Figure 9:
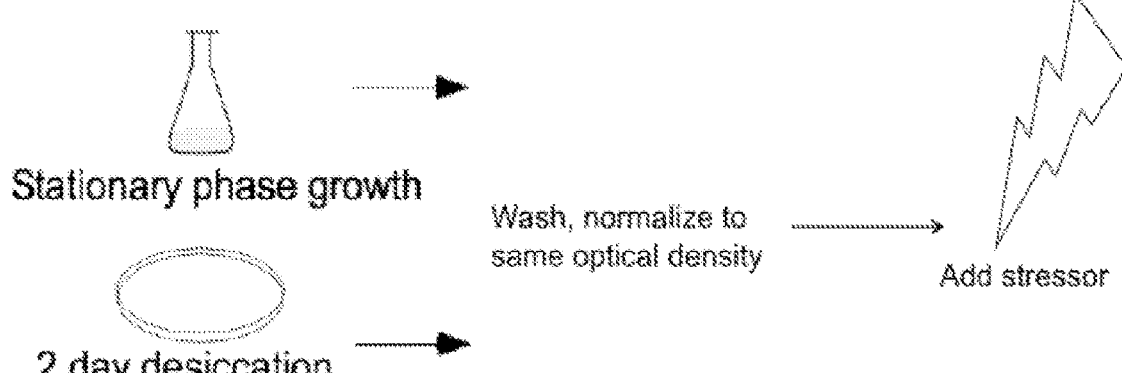

FIG. 9 shows a schematic illustrating desiccation stress tolerance assays.

Figures 10, 11:
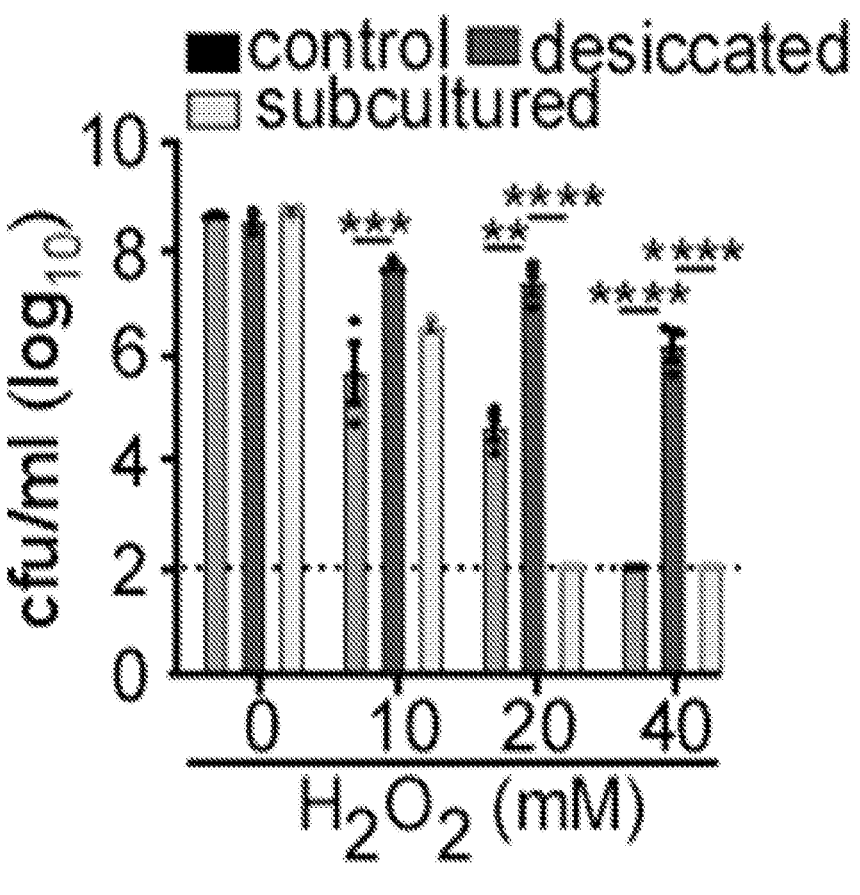

FIG. 10 shows a graph illustrating that desiccated *A. baumannii* is pre-adapted to $H_2O_2$ stress and subculture reverses resistance.

FIG. 11 shows a schematic illustrating a Tn-Seq screen to identify genes involved in desiccation survival.

Figure 12:
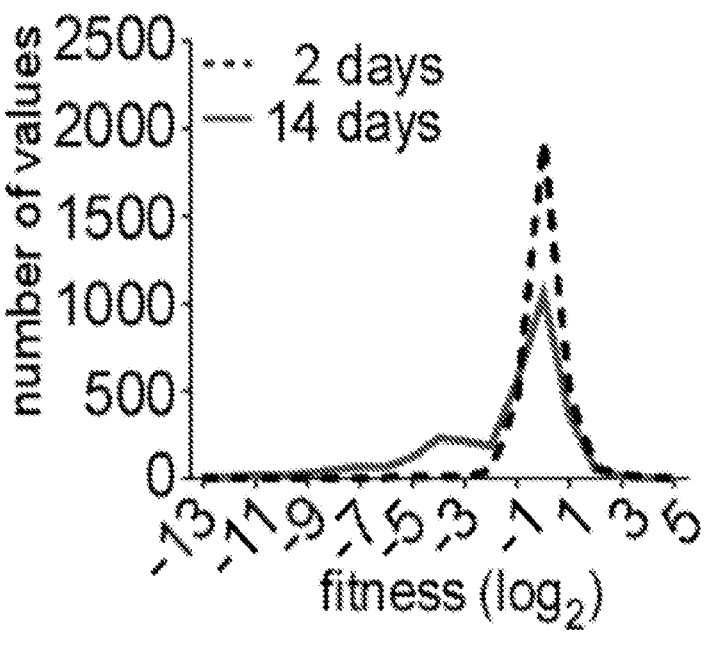

FIG. 12 shows a graph illustrating gene products influencing desiccation tolerance in *A. baumannii*.

Figure 13:
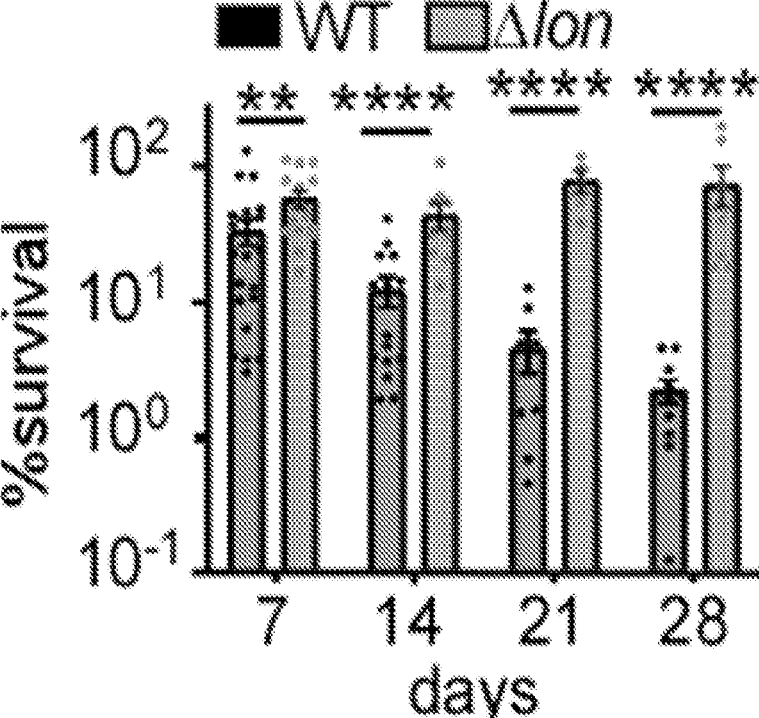

FIG. 13 shows a graph illustrating desiccation tolerance of wild type and Δlon mutant.

Figure 14:
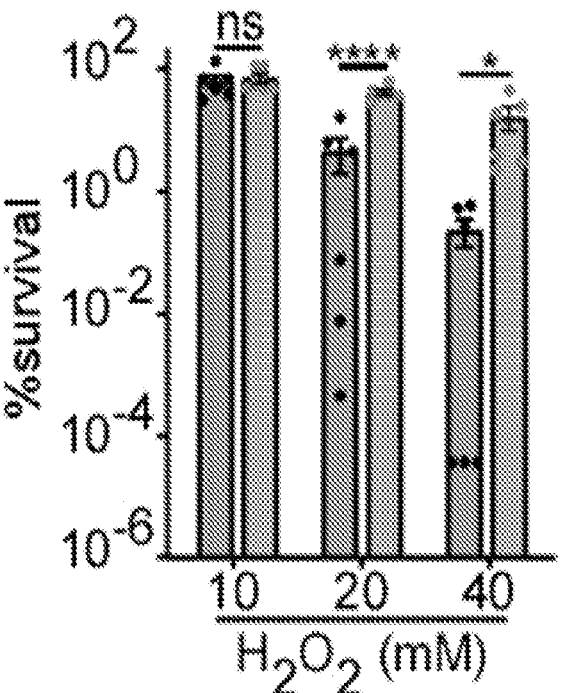

FIG. 14 shows a graph illustrating oxidative stress resistance of wild type and Δlon mutant.

Figure 15:
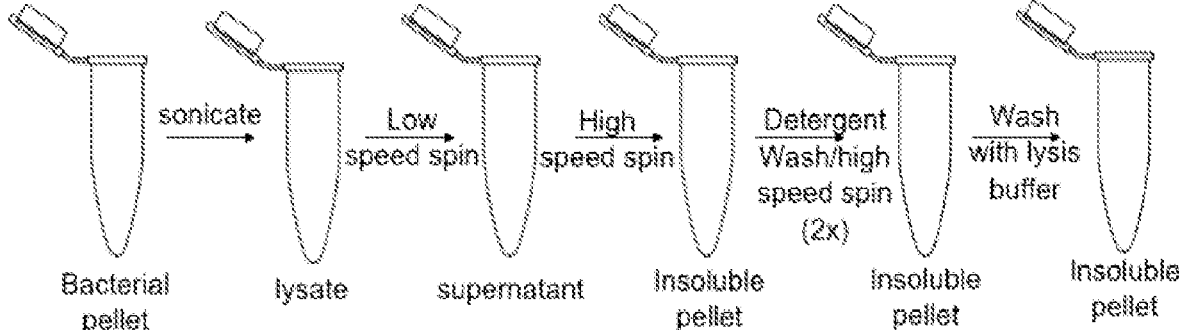

FIG. 15 shows a schematic illustrating formation of an insoluble pellet from a bacterial pellet.

Figure 16:
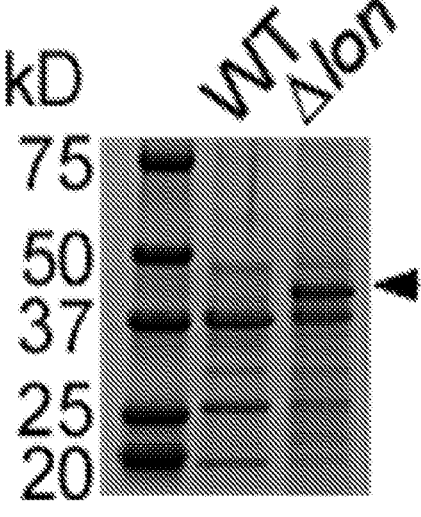

FIG. 16 shows an image illustrating protein species in the insoluble fraction of Δlon.

Figure 17:
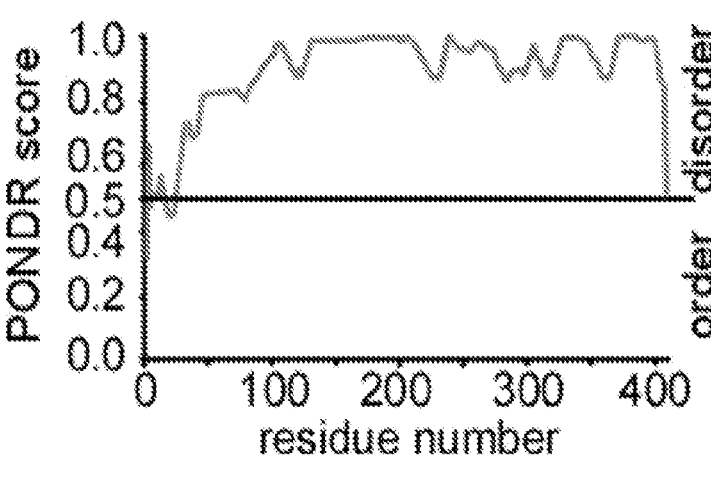

FIG. 17 shows a graph illustrating that dtpA is predicted to encode an intrinsically disordered protein.

Figure 18:
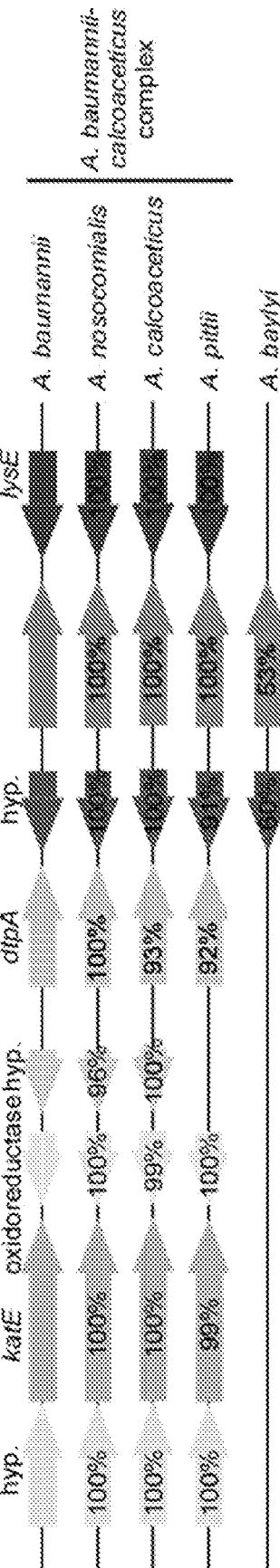

FIG. 18 shows an image illustrating that dtpA is conserved in the *A. calcoaceticus-A. baumannii* complex.

4

Figure 19:
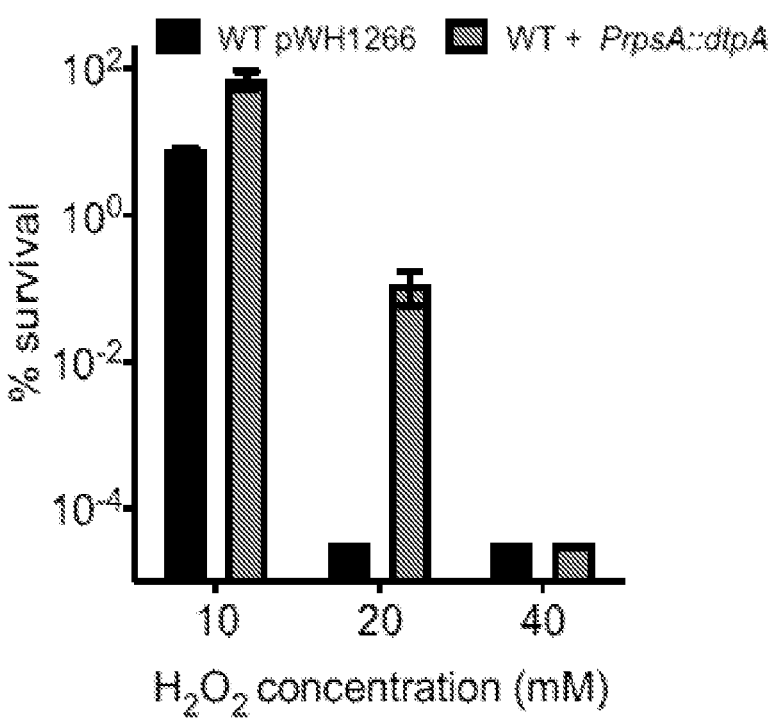

FIG. 19 shows a graph illustrating that dtpA overexpression enhances stress resistance in *A. Baumannii*.

Figure 20:
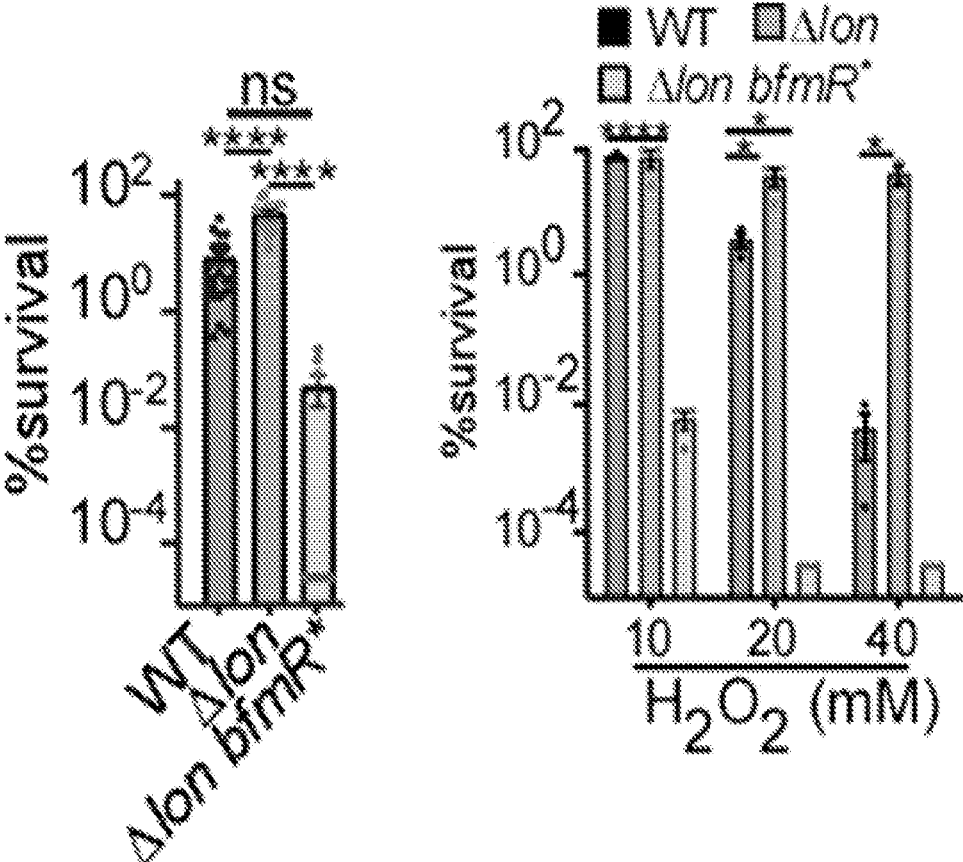

FIG. 20 shows graphs illustrating that the Δlon bfmR strain is sensitive to desiccation and $H_2O_2$.

FIG. 21 shows that a mutation in the Δlon bfmR strain mapped to the bfmR locus.

FIG. 22 shows an image illustrating that the Δlon bfmR strain does not produce DtpA in stationary phase.

FIG. 23 shows a graph illustrating that dtpA transcription is reduced in ΔbfmR strain.

Figure 24:
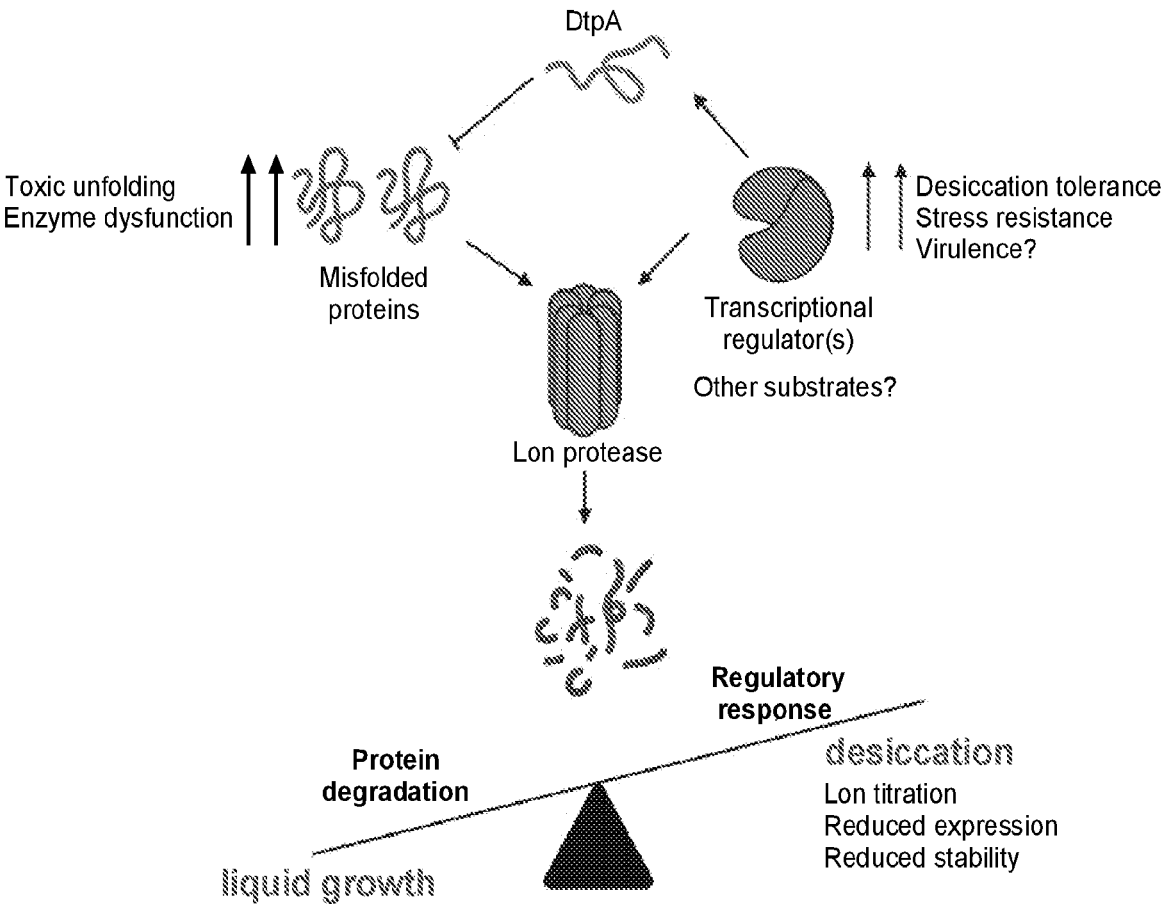

FIG. 24 shows a model for the relationship between environmental persistence and virulence in *A. baumannii*.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

BRIEF DESCRIPTION OF THE SEQUENCES

SEQ ID NO: 1 is an amino acid sequence for DtpA -
MANTRYEDDNNSSGTSNRGFASMDPERVREIASKGGRAAHASGNAHEFT

SEEAREAGRAAHASGNAHEFTSEEAREAGALSHKNDDRNGRGRSRYDDD

EDDDRGRSSGRGRGRSRYDDDDEDDDRGRSGGRGRGRSRDDDDEDDDRG

RSGGRGRGRSRDDDDEDDDRGRSGGRGRGRSRRDDDDEDDDRGRSGGRG

RGRSRRDDDDEDDDRGRSGGRGRGRSRYDDDDEDDDRGRSGGRGRGRSR

RDDDDEDDERGRSGGRGRGRSRRDDDDEDDERGRSGGRGRGRSRYDDDD

EDDDRGRSGGRGRGRSRYDDDDEDDDRGRSGGRGRGRSRRDDDDEDDDR

GRSGGRGRGRSRYDDDDEDDDRGRSGGRGRGRSRRDDDDDDDDRRGRSD

GRGQNSRNQKRDAYGRFTS.

Definitions

Unless defined otherwise, all technical and scientific terms used herein have the same meaning as commonly understood by one of ordinary skill in the art to which the disclosure belongs. Any methods and materials similar to or equivalent to those described herein can be used in the practice or testing of the present disclosure, including the methods and materials are described below.

Following long-standing patent law convention, the terms "a," "an," and "the" refer to "one or more" when used in this application, including the claims. Thus, for example, reference to "a cell" includes a plurality of cells, and so forth.

The terms "comprising," "including," and "having" are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "biologic" refers to any diagnostic, preventive, or therapeutic preparation derived from animal products or other biological sources.

All combinations of method or process steps as used herein can be performed in any order, unless otherwise specified or clearly implied to the contrary by the context in which the referenced combination is made.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter relates to articles and methods for protection against desiccation. In some embodiments, the article includes a recombinant nucleic acid construct. In some embodiments, the recombinant nucleic acid construct includes the nucleotide sequence encoding the amino acid sequence of accession number ACX60_11190 (SEQ ID NO: 1) or a complement thereof. In one embodiment, the complement nucleotide sequence includes at least 80% identity to the nucleotide sequence encoding the amino acid sequence of SEQ ID NO: 1. For example, in some embodiments, the complement nucleotide sequence includes one or more mutations in the disordered part of the protein, such as, but not limited to, nucleotides encoding the amino acids 26-411. In some embodiments, the article includes the amino acid sequence of SEQ ID NO: 1. In one embodiment, the amino acid sequence includes at least 80% identity to SEQ ID NO: 1. In some embodiments, the article includes a protein according to the amino acid sequence of SEQ ID NO: 1, referred to herein as DtpA. In one embodiment, the protein includes a protein having an amino acid sequence with at least 80% identity to SEQ ID NO: 1. In some embodiments, DtpA is an intrinsically disordered protein.

Without wishing to be bound by theory, it is believed that the protein, which is also referred to herein as DtpA, provides resistance to desiccation (drying out) of any suitable biologic for which drying out is a concern. Accordingly, also provided herein, in some embodiments, is a method of protecting one or more biologics from desiccation, the method including exogenously and/or recombinantly adding the DtpA to the biologic. In some embodiments, the method includes forming a composition including at least one biologic and the DtpA. In one embodiment, the composition is a solid composition. In one embodiment, the composition is a liquid composition.

Suitable biologics include, but are not limited to, enzymes, food, vaccines, heterologous polypeptides, heterologous proteins, or combinations thereof. As used herein, the terms "heterologous polypeptides" and "heterologous proteins" refers to polypeptides and/or proteins expressed in an organism that is not *Acinetobacter baumannii*. For example, in one embodiment, the method includes recombinantly and/or exogenously adding the DtpA to purified enzymes, the DtpA protecting the enzymes from drying out. In one embodiment, the method includes recombinantly and/or exogenously adding the DtpA to at least one heterologous polypeptide or protein of interest. In another embodiment, the DtpA stabilizes the at least one heterologous polypeptide or protein of interest. As used herein, stabilizing a heterologous polypeptide or protein means maintaining the structure under aqueous and dry conditions, or after being frozen and or dried and then rehydrated.

Additionally or alternatively, in some embodiments, when the DtpA is expressed in organisms other than *Acinetobacter baumannii* it confers resistance to desiccation upon those organisms. Without wishing to be bound by theory, it is believed that the DtpA protects against protein misfolding/aggregation, which is a common consequence of desiccation in different organisms/cell types. Accordingly, further provided herein, in some embodiments, is a method of stabilizing a heterologous organism, such as, but not limited to, a plant or animal cell, bacteria, probiotic, tissue, organ, and/or plant. In some embodiments, the method includes contacting the heterologous organism with a formulation comprising DtpA. In one embodiment, the formulation includes the DtpA. In another embodiment, the formulation includes a composition including the DtpA. In some embodiments, the method includes endogenously expressing the DtpA in the heterologous organism. In one embodiment, the method includes producing a transgenic cell or organism by introducing the nucleotide sequence encoding the amino acid sequence of SEQ ID NO: 1 into the heterologous cell or organism. For example, in another embodiment, dtpA is cloned into the eukaryotic expression vector pCMV6 and introduced into Cos-7 fibroblast cells or other suitable cells through transient transfection. In another embodiment, the method includes introducing dtpA into bacteria strains belonging to the gut microbiota that are frequently included in commercial probiotic supplements using plasmid expression constructs.

In some embodiments, the exogenous addition and/or endogenous expression of DtpA stabilizes the heterologous plant or animal cell, bacteria, probiotic, tissue, organ, and/or plant. As used herein, stabilizing a cell, bacteria, probiotic, tissue, organ, and/or plant, means maintaining the structure and function thereof a under aqueous or dry conditions, or after being frozen and dried and then rehydrated. In some embodiments, the exogenous addition and/or endogenous expression of DtpA provides an organism with increased tolerance to desiccation. An increased tolerance to desiccation refers to the ability of a protein, cell, tissue, organ, or organism that has either had contact with DtpA, or has been transformed with the heterologous nucleotide sequence encoding DtpA, to tolerate water loss, drought, or being frozen and dried and then rehydrated, better than a control protein, cell, tissue, organ, or organism. An isolated cell refers to either 1) a single-celled organism such as a bacterium or yeast, or 2) a cell that is separated from other components with which it is normally associated in its natural state. An organ or tissue may include, but is not limited to, lungs, lymph nodes, pharynx, larynx, heart, liver, gallbladder, kidneys, bone, large intestines, small intestines, urinary bladder, pancreas, stomach, spleen, skin, nervous tissue, epithelial tissue, connective tissue, muscle tissue, stem, leaf, petal, stamen, pistil, root, seed, pollen, flower, fruit, ovule, sepal, bud, anther, filament, ovary, stigma, pedicle.

Additionally or alternatively, in some embodiments, when the DtpA is expressed in organisms other than *Acinetobacter baumannii* it confers resistance to heat upon those organisms. Accordingly, also provided herein, in some embodiments, is a method of protecting a heterologous organism (e.g., a plant or animal cell, bacteria, probiotic, tissue, organ, and/or plant) from heat. As used herein, protecting a cell, bacteria, probiotic, tissue, organ, and/or plant from heat means maintaining the structure and function thereof under elevated temperature conditions, such as, but not limited to, temperatures of up to 65° C. (150° F.). Without wishing to be bound by theory, it is believed that the DtpA protects against protein misfolding/aggregation resulting from exposure of different organisms/cell types to high temperatures. For example, in one embodiment, the exogenous addition and/or endogenous expression of DtpA crops from elevated heat. In another embodiment, the exogenous addition and/or endogenous expression of DtpA facilitates the delivery of vaccines and medicines by protecting the vaccine/medicine from elevated heat during transportation and/or storage.

In some embodiments, the method of protecting a heterologous organism from heat includes contacting the heterologous organism with a formulation comprising DtpA. In one embodiment, the formulation includes the DtpA. In another embodiment, the formulation includes a composition including the DtpA. In some embodiments, the method includes endogenously expressing the DtpA in the heterologous organism. In one embodiment, the method includes producing a transgenic cell or organism by introducing the nucleotide sequence encoding the amino acid sequence of SEQ ID NO: 1 into the heterologous cell or organism. For example, in another embodiment, dtpA is cloned into the eukaryotic expression vector pCMV6 and introduced into Cos-7 fibroblast cells or other suitable cells through transient transfection. In another embodiment, the method includes introducing dtpA into bacteria strains belonging to the gut microbiota that are frequently included in commercial probiotic supplements using plasmid expression constructs.

The articles and methods disclosed herein overcome the current shortcomings in the shelf-stabilization of protein- and live-bacterial based therapeutics by providing new protein-based compositions and methods for stabilizing proteins and other biological material.

The presently-disclosed subject matter is further illustrated by the following specific but non-limiting examples. The following examples may include compilations of data that are representative of data gathered at various times during the course of development and experimentation related to the presently-disclosed subject matter.

Examples

This Example discusses the identification and verification of gene products that influence desiccation tolerance.

Referring to FIGS. 4-5, the impact of growth phase on desiccation tolerance was first explored. As illustrated in FIG. 5, it was found that stationary growth phase provided increased desiccation survival as compared to exponential growth phase. In view thereof, the impact of desiccation on virulence was explored by employing a murine model using stationary growth phase and two day desiccated *A. baumannii* 17978 (FIG. 6). The desiccated *A. baumannii* 17978 was more virulent (FIG. 7) and showed enhanced bacterial loads following infection (FIG. 8). To determine how desiccation effects stress tolerance, stationary growth phase and two day desiccated *A. baumannii* were washed and normalized to the same optical density, then a stressor was added (FIG. 9). As illustrated in FIG. 10, the desiccated *A. baumannii* was pre-adapted to $H_2O_2$ stress, while subculture reversed the resistance. A Tn-Seq screen was then used to identify genes that influence desiccation survival (FIG. 11). The fitness of the gene products is shown in FIG. 12.

The ATP-dependent AAA+ lon proteases degrade aggregated/misfolded proteins. They were first identified in *E. coli*, but are conserved in a large variety of prokaryotes as well as in eukaryotes (in mitochondria). The lon proteases contain 3 domains: substrate recognition, ATP binding, and proteolytic, and degrade naturally unstable proteins that are involved in a great variety of biological processes. In other bacterial organisms, loss of lon is usually associated with stress sensitivity (heat shock and starvation). However, the Δlon mutant exhibits increased desiccation tolerance and oxidative stress resistance (FIGS. 13-14). In view thereof, the present inventors explored whether aggregated proteins were promoting desiccation tolerance of Δlon mutant (FIG. 15). As illustrated in FIG. 16, an approximately 45 kD protein species was enriched in the insoluble fraction of Δlon. This protein was identified as ACX60_11190: "Stress-induced protein" (SEQ ID NO: 1).

ACX60_11190 is predicted to encode an intrinsically disordered protein (IDP) (FIG. 17). Since IDPs are associated with desiccation tolerance in tardigrades and plants, the present inventors next explored how IDPs protect from desiccation. There are two leading hypotheses for this protection—vitrification: because IDPs do not fold, they could form glass like solids in response to desiccation that could protect or "shield" other proteins; or water replacement: charged IDPs form hydrogen bonds with cellular components in place of water.

As illustrated in FIG. 18, ACX60_11190 is conserved in the pathogenic *A. calcoaceticus-A. baumannii* complex. Additionally, as shown in FIGS. 1A-B, the present inventors found that deletion of ACX60_11190 abrogates accumulation of 45 kD protein WT and Δlon strains (FIG. 1A), and that ACX60_11190 is required for desiccation tolerance (FIG. 1B). Furthermore, it was found that dtpA overexpression enhances stress resistance in *A. baumannii* (FIGS. 2A and 19) and that dtpA overexpression in *E. coli* enhances desiccation tolerance (FIG. 2B).

To determine how the production of DtpA is regulated in response to desiccation, phenotypic variants of Δlon mutant were isolated on LB agar. As shown in FIG. 20, the Δlon suppressor strain (Δlon bfmR*) is sensitive to desiccation and $H_2O_2$. The mutation in the Δlon suppressor strain is mapped to the bfmR locus (FIG. 21) and does not produce DtpA in stationary phase (FIG. 22). Additionally, dtpA transcription is reduced in the Δlon bfmR* strain (FIG. 23).

Based upon the data above, the present inventors developed the model shown in FIG. 24 for the relationship between environmental persistence and virulence in *A. baumannii*.

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

---

What is claimed is:

1. A composition, comprising:
   a DtpA protein comprising the sequence of SEQ ID NO: 1; and
   a heterologous protein.

2. The composition of claim 1, wherein the composition is solid.

3. The composition of claim 1, wherein the composition is liquid.

4. The composition of claim 1, wherein the DtpA protein is recombinantly expressed and added to the heterologous protein.

5. The composition of claim 1, wherein the DtpA protein and the heterologous protein are expressed in an organism that is not *Acinetobacter baumannii*.

6. A method of protecting a heterologous protein against protein misfolding or aggregation, the method comprising contacting the heterologous protein with a DtpA protein comprising the sequence of SEQ ID NO: 1.

7. The method of claim 6, wherein the heterologous protein is an enzyme.

8. The composition of claim 1, wherein the heterologous protein is an enzyme.

9. The composition of claim 1, wherein a heterologous biologic selected from the group consisting of food and vaccine comprises the heterologous protein.

10. The method of claim 6, wherein a heterologous biologic selected from the group consisting of food and vaccine comprises the heterologous protein.

* * * * *

```
                          SEQUENCE LISTING

<160> NUMBER OF SEQ ID NOS: 1

<210> SEQ ID NO 1
<211> LENGTH: 411
<212> TYPE: PRT
<213> ORGANISM: Acinetobacter baumannii

<400> SEQUENCE: 1

Met Ala Asn Thr Arg Tyr Glu Asp Asp Asn Asn Ser Ser Gly Thr Ser
1               5                   10                  15

Asn Arg Gly Phe Ala Ser Met Asp Pro Glu Arg Val Arg Glu Ile Ala
                20                  25                  30

Ser Lys Gly Gly Arg Ala Ala His Ala Ser Gly Asn Ala His Glu Phe
            35                  40                  45

Thr Ser Glu Glu Ala Arg Glu Ala Gly Arg Ala Ala His Ala Ser Gly
        50                  55                  60

Asn Ala His Glu Phe Thr Ser Glu Glu Ala Arg Glu Ala Gly Ala Leu
65                  70                  75                  80

Ser His Lys Asn Asp Asp Arg Asn Gly Arg Gly Arg Ser Arg Tyr Asp
                85                  90                  95

Asp Asp Glu Asp Asp Asp Arg Gly Arg Ser Ser Gly Arg Gly Arg Gly
            100                 105                 110

Arg Ser Arg Tyr Asp Asp Asp Asp Glu Asp Asp Asp Arg Gly Arg Ser
            115                 120                 125

Gly Gly Arg Gly Arg Gly Arg Ser Arg Asp Asp Asp Asp Glu Asp Asp
        130                 135                 140

Asp Arg Gly Arg Ser Gly Gly Arg Gly Arg Gly Arg Ser Arg Asp Asp
145                 150                 155                 160

Asp Asp Glu Asp Asp Asp Arg Gly Arg Ser Gly Gly Arg Gly Arg Gly
            165                 170                 175

Arg Ser Arg Arg Asp Asp Asp Asp Glu Asp Asp Asp Arg Gly Arg Ser
            180                 185                 190

Gly Gly Arg Gly Arg Gly Arg Ser Arg Arg Asp Asp Asp Asp Glu Asp
        195                 200                 205

Asp Asp Arg Gly Arg Ser Gly Gly Arg Gly Arg Gly Arg Ser Arg Tyr
        210                 215                 220

Asp Asp Asp Asp Glu Asp Asp Asp Arg Gly Arg Ser Gly Gly Arg Gly
225                 230                 235                 240

Arg Gly Arg Ser Arg Arg Asp Asp Asp Glu Asp Asp Glu Arg Gly
                245                 250                 255

Arg Ser Gly Gly Arg Gly Arg Gly Arg Ser Arg Arg Asp Asp Asp Asp
            260                 265                 270

Glu Asp Asp Glu Arg Gly Arg Ser Gly Gly Arg Gly Arg Gly Arg Ser
            275                 280                 285

Arg Tyr Asp Asp Asp Asp Glu Asp Asp Asp Arg Gly Arg Ser Gly Gly
        290                 295                 300

Arg Gly Arg Gly Arg Ser Arg Tyr Asp Asp Asp Asp Glu Asp Asp Asp
305                 310                 315                 320

Arg Gly Arg Ser Gly Gly Arg Gly Arg Gly Arg Ser Arg Arg Asp Asp
        325                 330                 335
```

-continued

```
Asp Asp Glu Asp Asp Asp Arg Gly Arg Ser Gly Gly Arg Gly Arg Gly
            340             345             350

Arg Ser Arg Tyr Asp Asp Asp Asp Glu Asp Asp Asp Arg Gly Arg Ser
        355             360             365

Gly Gly Arg Gly Arg Gly Arg Ser Arg Arg Asp Asp Asp Asp Asp Asp
    370             375             380

Asp Asp Arg Arg Gly Arg Ser Asp Gly Arg Gly Gln Asn Ser Arg Asn
385             390             395             400

Gln Lys Arg Asp Ala Tyr Gly Arg Phe Thr Ser
            405             410
```